United States Patent [19]

Falk et al.

[11] 4,419,298
[45] Dec. 6, 1983

[54] ETHANOLAMINE SALTS OF DI-PERFLUOROALKYL GROUP CONTAINING ACIDS

[75] Inventors: Robert A. Falk, New City; István Borsodi, Yonkers, both of N.Y.; Dieter Reinehr, Kandern, Fed. Rep. of Germany

[73] Assignee: Ciba-Geigy Corporation, Ardsley, N.Y.

[21] Appl. No.: 292,326

[22] Filed: Aug. 12, 1981

[51] Int. Cl.³ .............................................. C07C 53/18
[52] U.S. Cl. ........................ 260/501.16; 260/501.15; 260/501.12; 260/501.13; 252/311; 106/2
[58] Field of Search .................. 260/501.17, 501.15, 260/501.16

[56] References Cited

U.S. PATENT DOCUMENTS

| | | | |
|---|---|---|---|
| 2,144,552 | 1/1939 | Shonie | 260/501.17 |
| 2,278,499 | 4/1942 | Smith et al. | 260/501.17 |
| 2,753,372 | 7/1956 | Lundberg | 260/501.17 |
| 2,762,842 | 9/1956 | Hafliger et al. | 260/501.17 X |
| 2,843,471 | 7/1958 | Fischer | 260/501.17 X |
| 2,976,316 | 3/1961 | Boresch et al. | 260/501.17 |
| 4,239,915 | 12/1980 | Falk | 562/481 |

OTHER PUBLICATIONS

Sidgwick, The Organic Chemistry of Nitrogen (1966) 105-106.

*Primary Examiner*—Bernard Helfin
*Attorney, Agent, or Firm*—Michael W. Glynn

[57] ABSTRACT

Ammonium and amine salts of acids having the formula

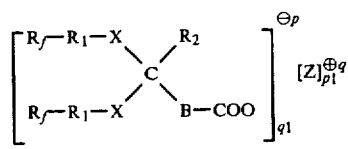

wherein $R_f$ is a perfluoroalkyl group; $R_1$ is alkylene or substituted alkylene; X is —S—, —SO—, or —SO$_2$—; $R_2$ is hydrogen, alkyl, aryl, substituted aryl, —B—COOH or a —B—COO anion; B is a covalent bond, arylene or alkylene; Z is the ammonium or amine cation; p is the anionic charge, q is the cationic charge; and $p_1$ and $q_1$ are the balanced mole equivalents respectively, are provided. These salts applied in the form of aqueous dispersions or emulsions, are useful in rendering cellulosic and natural and synthetic polyamide materials oil and water repellent.

4 Claims, No Drawings

ETHANOLAMINE SALTS OF DI-PERFLUOROALKYL GROUP CONTAINING ACIDS

BACKGROUND OF THE INVENTION

The instant invention is directed to salts of di-perfluoroalkyl group containing acids with ammonia or amines, and the manufacture and use of such salts in the form of aqueous emulsions or dispersions in treating cellulosic materials and natural polyamide materials to render the same oil and water repellent.

Di-perfluoroalkyl group containing acids, useful as starting materials in the manufacture of the instant ammonium and amine salts, are, in part, disclosed in U.S. Pat. No. 4,239,915, the disclosure of which is incorporated by reference herein. The di-perfluoroalkyl group containing acids are disclosed therein as useful inter alia for textile treating or as chromium complexes which possess oil and water repellent properties and are indicated as useful as grease or oil repellents for paper. Unfortunately, these acids possess, in general, very limited water solubility and therefore require an organic solvent, or the like, for the application of the di-perfluoroalkyl group containing acids to the cellulose, synthetic or natural polyamide substrate in order to obtain the desired oil and water repellent properties. Such organic solvent containing solutions of the di-perfluoroalkyl group containing acids tend to be expensive due to the cost of such organic solvents. Moreover, the use of such organic solvent containing systems is often undesirable due to odor, toxicity and flammability hazards. Furthermore, such organic solvent containing systems tend to be inefficient since much of the fluorochemical tends to remain in the organic solvent system during the application process and must be subsequently recovered from the spent organic solvent liquor for re-use. Also environmental problems are usually inherent in the use of organic solvent systems on an industrial scale.

It is an object of the present invention to avoid such problems by providing to the artisan ammonium and amine salts of di-perfluoroalkyl group containing acids. The ammonium and amine salts of the present invention are conveniently prepared by reacting the corresponding di-perfluoroalkyl group containing acids with ammonia or the amine in a diluent substantially inert to the acid and ammonia or amine reactants, and recovering the amine salt formed. As the reaction between the ammonia or amine and the acid takes place spontaneously, the reaction can be conducted at temperatures between 0° C. and 100° C., preferably at ambient temperature conditions. Where the amine is introduced in gaseous form, such as anhydrous ammonia or methyl amine, it can be bubbled through the acid in the liquid diluent medium. As the reaction tends to be exothermic, cooling of the reaction vessel may be advantageously employed. Where the inert diluent is organic in nature, such as a lower alkanol, for example methanol, isopropanol, or the like, the ammonium or amine salt reaction product can be recovered by precipitation, or evaporation of the diluent. If the inert diluent is water, the ammonium or amine salt need not be separated from the aqueous media.

Where the amine is a quaternary ammonium compound, the resulting salt may be obtained by adding together in the inert diluent, such as water, the di-perfluoroalkyl group containing acid with the quaternary ammonium compound in the base, or hydroxide form. Alternatively, the di-perfluoroalkyl group containing acid may be neutralized with alkali or alkaline earth metal base, and the metal salt reacted with the quaternary ammonium compound in the halide form in an inert diluent by double displacement and the inorganic salt optionally separated therefrom by known extraction or precipitation techniques.

It is a further object of the invention to provide to the artisan aqueous emulsions and dispersions of the ammonium and amine salts which avoid the application problems associated with organic solvent containing systems.

It is a further object of the present invention to provide the artisan with efficient fluorochemical dispersions and emulsions providing high fluorochemical pick-up properties on cellulosic and natural polyamide substrates.

It is a further object of the present invention to provide the artisan with fluorochemical treated cellulosic and natural polyamide containing materials possessing a high degree of oil and water repellent properties, and a method of making the same.

These and other objects of the invention are apparent from the foregoing disclosure.

DETAILED DISCLOSURE

One aspect of the instant invention relates to ammonium and amine salts of gem-perfluoroalkyl group containing acids of the formula

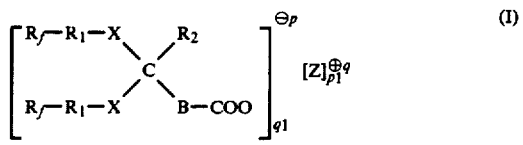

wherein $R_f$ is perfluoroalkyl of 4 to 18 carbon atoms or perfluoroalkoxy-perfluoroalkyl of 4 to 18 carbon atoms;

$R_1$ is straight or branched chain alkylene of 1 to 12 carbon atoms, alkylenethioalkylene of 2 to 12 carbon atoms, alkyleneoxyalkylene of 2 to 12 carbon atoms, or alkyleneiminoalkylene of 2 to 12 carbon atoms where the imino nitrogen atom contains as a third substituent, hydrogen or alkyl of 1 to 6 carbon atoms;

X is —S—, —SO— or —SO$_2$—;

$R_2$ is hydrogen, straight or branched chain alkyl of 1 to 6 carbon atoms, phenyl, alkyl substituted phenyl of up to 18 carbon atoms, or is the carboxylic acid group —B—COOH, or the carboxylate anion —B—COO;

B is a covalent bond, or alkylene of up to 18 carbon atoms, phenylene, phenoxyalkylene of 7 to 14 carbon atoms, phenylalkylene of 7 to 14 carbon atoms, phenylalkylene of 7 to 14 carbon atoms, phenyalkenylene of 8 to 14 carbon atoms, or phenylene substituted by alkyl of 1 to 4 carbon atoms;

Z is the ammonium or amine cation;

p is the anionic charge of the gem-perfluoroalkyl group containing acid and is 1 or 2;

q is the cationic charge of the ammonium or amine group, Z, and has a value of 1 to 200; and the cationic mole equivalent, $p_1$ is equal to p and the anion mole equivalent, $q_1$, is equal to q, with the proviso that where p is 2 and q is an even integer, then $p_1$ is 1 and $q_1$ is q/2.

Preferably $R_f$ is perfluoroalkyl of 6 to 14 carbon atoms, $R_1$ is straight or branched chain alkylene of 2 to 8 carbon atoms, X is —S— or —SO$_2$—, $R_2$ is hydrogen or alkyl of 1 to 4 carbon atoms, —B— is a covalent bond or alkylene of 1 to 6 carbon atoms, p is 1 and q is 1 to 4. In a more preferred embodiment, X is —S— and q is 1 or 2.

Most preferably $R_f$ is perfluoroalkyl of 6 to 12 carbon atoms, $R_1$ is alkylene of 2 to 4 carbon atoms, X is —S— or —SO$_2$—, $R_2$ is hydrogen or alkyl of 1 to 2 carbon atoms, —B— is a covalent bond or alkylene of 1 to 3 carbon atoms, p is 1 and q is 1 or 2.

Z is preferably the cation of ammonia, or of a water soluble mono- or polyamine. Most preferably, Z is the cation of a water soluble mono- or polyamine having a water solubility at 25° C. of at least 2% by weight in water.

Preferably, the amine cation is a cation of such a water soluble amine having the formula

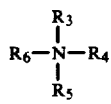
(II)

wherein $R_3$ is hydrogen, alkyl of 1 to 5 carbon atoms; alkyl of 2 to 6 carbon atoms substituted by 2 to 6 hydroxy groups; alkenyl of 3 to 5 carbon atoms; cycloalkyl of 5 to 7 carbon atoms; —C$_1$—C$_3$—alkylene—COOH;

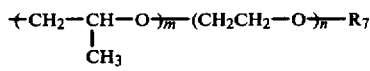

where m is 0 to 6, n is 0 to 30, and $R_7$ is hydrogen, alkyl of 1 to 3 carbon atoms or alkanoyl of 2 to 4 carbon atoms; or is

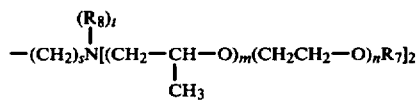

wherein s is 2 to 6, $R_8$ is hydrogen or alkyl of 1 to 3 carbon atoms, t is 0 or 1 and m, n and $R_7$ are as above defined; or is

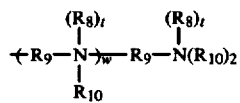

where $R_9$ is straight or branched chain alkylene of 2 to 8 carbon atoms, cyclohexylene or di(C$_1$ to C$_3$-alkylene)-cyclohexylene, w is 0 to 198, $R_{10}$ is hydrogen, alkyl of 1 to 3 carbon atoms, alkyl of 2 to 6 carbon atoms substituted by hydroxy, or C$_1$—C$_3$—alkylene—COOH, and $R_8$ and t are defined above; or is

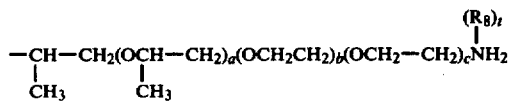

where a is 1 to 20, b is 2 to 50, c is 2 to 20 and $R_8$ and t are as defined above;

$R_4$ and $R_5$ are independently hydrogen, alkyl of 1 to 5 carbon atoms or

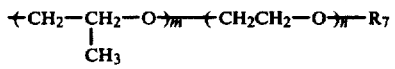

where m, n and $R_7$ are as defined above; or $R_4$ and $R_5$ taken together with the nitrogen to which they are attached represent morpholino; and $R_6$ is alkyl of 1 to 5 carbon atoms; hydrogen when at least one of $R_3$, $R_4$ and $R_5$ is other than hydrogen; alkyl of 6 to 23 carbon atoms when $R_3$ is other than hydrogen or alkyl of 1 to 5 carbon atoms;

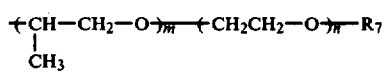

where m, n and $R_7$ are as defined above; or $R_4$, $R_5$ and $R_6$, taken together with the nitrogen which they are attached represent pyridyl; with the proviso that the total value of t equals q-1.

In a more preferred embodiment, $R_3$ is of the formula (CH$_2$CH$_2$—O)$_n$ H where n is 1 to 10, $R_4$ and $R_5$ is hydrogen or (CH$_2$CH$_2$—O)$_n$ H where n is 1 to 10 and $R_6$ is hydrogen, or (CH$_2$CH$_2$—O)$_n$ H where n is 1 to 10. Most preferably, n is 1 in each case.

Another more preferred embodiment, $R_3$ is of the formula (CH$_2$CH$_2$—O)$_n$ H where n is 1 to 10, $R_4$ is (CH$_2$CH$_2$—O)$_n$ H where n is 1 to 10, $R_5$ is hydrogen or (CH$_2$CH$_2$—O)$_n$ H where n is 1 to 10 and $R_6$ is alkyl of 6 to 20 carbon atoms. Most preferably, in this embodiment, the total value of n should be greater than 3 in order to insure the desired solubility of the amine.

Advantageously, the solubility of the amine in water is determined on the basis of free amine in water, or in the case of quaternary ammonium compounds, as the quaternary chloride.

In preparing the instant amine salts from polyamines, one may utilize one or more equivalents of gem-perfluoroalkyl group containing acid per mole of polyamine. Thus, where Z in formula I is a polyamine, one or more amine nitrogens may be protonated, corresponding to the cationic charge, q. In the preferred embodiment of the amine cation in formula II, therefore, each additional protonated amine nitrogen, other than the nitrogen directly bonded to $R_3$, $R_4$, $R_5$ and $R_6$, is represented by the presence of an $R_8$ group, i.e. where t equals 1 as to such amine nitrogen. Accordingly, the total number of protonated amine nitrogens is q, and the value of t equals q-1. Similarly, the value of p, corresponding to the anionic charge in formula I, is 2 when $R_2$ is the carboxylate anion —B—COO, and is 1 where $R_2$ is other than —B—COO.

The cation mole equivalent in formula (I), $p_1$, is equal to the charge of its counter ion, i.e. the anionic charge p, and the anion mole equivalent $q_1$ is equal to the charge of its counter ion, the cationic charge q; except where p is 2 and q is an even integer, then $p_1$ is 1 and $q_1$ is q/2. Thus, for example, where the anion charge p is 2 and the cationic charge q is 3, then the balanced formula (I) contains 2 equivalents of Z, or $p_1$ is 2, and 3 equivalents of the acid anion, or $q_1$ is 3. Of course, where both the cation, Z, and the acid anion are both divalent, i.e. p and q are each 2, then there is one mole equivalent of acid anion per mole equivalent of cation, or $p_1$ is 1, and $q_1$ is 2/2 or 1.

Examples of highly advantageous amine cations include $\overset{\oplus}{H_3N}CH_2CH_2OH$, $\overset{\oplus}{H_2N}(CH_2CH_2OH)_2$, $\overset{\oplus}{HN}(CH_2CH_2OH)_3$, $$R-\overset{\oplus}{\underset{\phantom{|}}{N}}-H \begin{matrix} (CH_2CH_2O)_xH \\ \\ (CH_2CH_2O)_yH \end{matrix}$$

where R is coco fatty alkyl and x+y is about 15, $$R-\overset{\oplus}{\underset{\phantom{|}}{N}}-H \begin{matrix} (CH_2CH_2O)_xH \\ \\ (CH_2CH_2O)_yH \end{matrix}$$

where R is steary and x+y is about 15, $$R-\overset{\oplus}{\underset{\phantom{|}}{N}}\begin{matrix} (CH_2CH_2O)_{\overline{x}}H \\ (CH_2CH_2O)_{\overline{y}}H \\ (CH_2CH_2O)_{\overline{z}}H \end{matrix}$$

where R is tallow and x+y+z is about 10, $$(CH_3)_2-\underset{\underset{H}{\overset{\oplus}{N}(CH_3)_2}}{\overset{|}{C}}-CH_2OH$$

$\overset{\oplus}{N}(CH_3)_4$, $\overset{\oplus}{N}(CH_2CH_2OH)_4$, $$(CH_3)_2-\underset{\underset{H}{\overset{\oplus}{N}(CH_3)_2}}{\overset{|}{C}}-CH_2OH$$

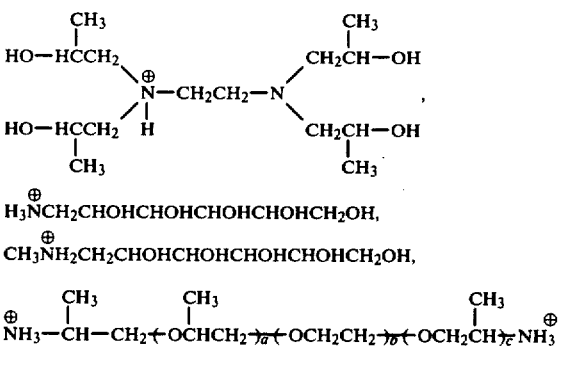

$\overset{\oplus}{H_3N}CH_2CHOHCHOHCHOHCHOHCH_2OH$, $\overset{\oplus}{CH_3NH_2}CH_2CHOHCHOHCHOHCHOHCH_2OH$, $$\overset{\oplus}{NH_3}-\overset{\overset{CH_3}{|}}{CH}-CH_2(OCHCH_2)_{\overline{a}}(OCH_2CH_2)_{\overline{b}}(OCH_2\overset{\overset{CH_3}{|}}{CH})_{\overline{c}}\overset{\oplus}{NH_3}$$

where a+c is 2 to 30 and b is 5 to 40, $\overset{\oplus}{H_3N}-CH_2CH_2CH_2\overset{\oplus}{NH_3}$, $$R-\underset{\underset{(CH_2CH_2O)_xH}{|}}{\overset{\overset{H\oplus}{|}}{N}}-CH_2CH_2-\overset{\overset{H}{|}}{\underset{\underset{(CH_2CH_2O)_2H}{|}}{N}}\overset{(CH_2CH_2O)_yH}{\underset{\phantom{|}}{\oplus}}$$

where R is coco fatty alkyl and x+y+z is about 10, $\overset{\oplus}{HN}(CH_2COOH)_3$, and $(HOOCCH_2)_2\overset{\overset{\oplus}{N}}{\underset{H}{|}}-CH_2CH_2-\overset{\overset{\oplus}{N}}{\underset{H}{|}}(CH_2COOH)_2$.

Suitable amines which can be reacted with the gem-perfluoroalkyl containing acids to form useful salts include aminomethane, aminoethane, 1-aminopropane, 2-aminopropane, 1-aminobutane, 1-amino-2-methylpropane, 1,1-dimethylethylamine, 1-aminopentane, isoamylamine, tert-amylamine, allylamine, dimethylamine, diethylamine, diisopropylamine, trimethylamine, triethylamine, tri-n-butylamine, ethylenediamine, 1,2-propanediamine, trimethylenediamine, 1,3-diaminobutane, 1,4-diaminobutane, hexamethylene diamine, diethylenetriamine, triethylenetriamine, tetraethylene pentamine, polyethyleneimine having an average of about 20, 80, 120 or 200 units, diethylaminopropylamine, ethanolamine, diethanolamine, triethanolamine, ethylenediamine tetraacetic acid, nitrilotrisacetic acid, N-(hydroxyethyl)ethylenenediamine, N,N''-bis-(hydroxyethyl)-diethylenetriamine, N,N,N',N'-tetrakis-(2-hydroxypropyl)ethylenediamine N-(2-hydroxypropyl)-ethylene-diamine, cyclohexylamine, dicyclohexylamine, 1,8-diamino-p-menthane, and $$R-\underset{\underset{(CH_2CH_2O)_xH}{|}}{\overset{|}{N}}-CH_2CH_2CH_2N\begin{matrix}(CH_2CH_2O)_yH \\ \\ (CH_2CH_2O)_zH\end{matrix}$$

where R is tallow fatty alkyl and x+y+z is 3, 10 or 15.

Suitable perfluoroalkyl acids useful in preparing the instant salts include;

$(C_8F_{17}CH_2CH_2S)_2C(CH_3)CH_2CH_2COOH$, $(C_6F_{13}CH_2CH_2S)_2C(CH_3)CH_2CH_2COOH$, $(C_8F_{17}CH_2CH_2S)_2C(CH_3)COOH$, $(C_6F_{13}CH_2CH_2S)_2C(CH_2CH_2COOH)_2$, $[(CF_3)_2CFOCF_2CF_2CH_2CH_2S]_2C(CH_2CH_3)COOH$, $(C_8F_{17}CH_2CH_2OCH_2CH_2CH_2S)_2C(CH_3)CH_2COOH$, $(C_8F_{17}CH_2CH_2N(CH_3)CH_2CH_2S)_2C(CH_3)CH_2COOH$, $(C_8F_{17}CH_2CH_2SO_2)_2C(CH_3)COOH$,

$(C_8F_{17}CH_2CH_2S)_2CHC(CH_3)_2CH_2CH_2COOH$, and $(C_8F_{17}CH_2CH_2S)_2CHCOOH$.

The perfluoroalkyl acids useful in preparing the instant salts of formula I, where B is a covalent bond or alkylene can be prepared in the manner disclosed in U.S. Pat. No. 4,239,915. Those perfluoroalkyl acids useful in preparing the instant salts of formula I where B is phenylene, phenoxyalkylene of 7 to 14 carbon atoms, phenylalkenylene of 8 to 14 carbon atoms or phenylene substituted by alkyl of 1 to 4 carbon atoms are prepared in an analogous manner. Thus, two moles of mercaptan, $R_f$—$R_1$—SH is reacted per mole of either an aromatic aldehyde or ketone of the formula $R_2$—CO—B—COOH, optionally in the presence of a catalyst, such as hydrogen chloride or zinc chloride, or the corresponding acetal or ketal in the presence of boron trifluoride etherate. The reaction is easily carried out in an inert solvent such as an aliphatic or aromatic hydrocarbon, which may be chlorinated or fluorinated, or in the absence thereof. Suitable solvents include heptane, benzene, methylene chloride, 1,1,2-trifluoro-1,2,2-trichloroethylene, chlorobenzene and the like. Also ethers, such as ethylene glycol dimethyl ether or tetrahydrofuran may be used. The reaction mixture is advantageously kept at a temperature between room temperature and 80° C. under nitrogen until the reaction is completed. If desired, the resulting mercaptal, ($R_f$—$R_1$—S)$_2$C($R_2$)B—COOH, can be oxidized to the corresponding gem-sulfoxide and further, to the corresponding gem-sulfone by oxidation with the suitable oxidizing agent, such as nitric acid, peracetic acid, potassium monopersulfate, m-chloroperbenzoic acid and the like.

The gem-perfluoroalkyl group containing carboxylic acid amine salts are formulated as aqueous emulsion concentrates containing 5% to 40% by weight of the amine salt.

The aqueous emulsion concentrate is diluted to an application strength such that the emulsion contains 0.01% to 2% by weight, more preferably between 0.05% and 0.30% by weight of the amine salt, based on the weight of cellulosic or natural or synthetic polyamide substrate.

Suitable cellulosic and natural polyamide substrates for topical application include paper, non-woven fabrics, textiles, paperboard, wood, wood fiber products such as plywood, hair, including wool, hides, leather, and feathers. Synthetic polyamide substrates include nylon fibers and textiles.

For topical application, suitable aqueous emulsions contain, advantageously, 0.01% to 5%, preferably 0.02% to 2%, by weight of the amine salts at use dilution based on the weight of aqueous emulsion. Conventional adjuvants such as water repellant assistants, bacteriostats, coloring agents, surface conditioners and the like, may be included, e.g. in an amount of between about 0.01% and 5% by weight in the emulsion. Also, sizing agents, where the emulsion is to be used on cellulosic substrates, may be present in amounts of from 0.01% to 10% by weight.

The sizing agent may be a natural sizing agent such as animal glue, asphalt emulsions, wax emulsions, rosins, starches; a semisynthetic sizing agent such as a fatty acid salt or complex, a fortified rosin., e.g., tri sodium maleopimaric acid salt, sodium alginate or sodium carboxymethylcellulose; or a synthetic sizing agent such as an alkylketene dimer, alkylsuccinic anhydrides, polyvinyl alcohol, styrene-maleic anhydride polymers, and the like. Also mixtures thereof may be used.

Asphalt emulsions include those obtained from natural deposits or from the residue of crude petroleum distillation and emulsified in an aqueous solution with an emulsifier such as sodium rosinate or fatty amine. Wax emulsions include those prepared from paraffin waxes, optionally blended with rosin size and emulsified with a suitable emulsifier, such as guar gum, gum arabic, stearic acid salts, lignosulfonate salts, alkylamine salts, and the like. Starches include corn starch, potato starch, wheat starch, ethylated corn starch, cationic corn starch corn starch acetate, and the like. Fatty acid salts and complexes include, for example, stearic acid salts, e.g., of aluminum and zirconium, and the corresponding myristic acid, lauric acid, palmitic acid, margaric acid and behenic acid salts and the corresponding chromium complexes of these acids with chromium salts, including the Werner type complexes of a fatty acid, such as stearic or myristic acid with chromium chloride and isopropanol.

Alkylketene dimers include those wherein the alkyl group is between 6 to 23 carbon atoms such as the palmitic, stearic, oleic and myristic ketene dimers, as well as those where the alkyl group is unsaturated or branched chain, and mixtures thereof.

Alkylsuccinic anhydrides include those where the alkyl group is straight or branched chain and may be saturated or unsaturated having between about 6 to 23 carbon atoms, such as the n-hexadecenylsuccinic anhydride, the dodecylsuccinic anhydride, the dodecenylsuccinic anhydride, the isooctadecenylsuccinic anhydride, and the like.

Also alkylcarbamoyl chlorides, such as ditallowamine carbamoyl chloride; gelatins, cationic aqueous polyurethane emulsions, acrylic resins, stearyl amine surfactants, as known in the art, are suitable sizing agents.

Fillers include materials such as kaolin clay, calcium carbonate, alum, magnesium sulfate, sodium chloride, and the like.

Bacteriostats and fungicides are those commonly used in the paper, leather, fur and textile industries and include halogenated phenols, halogenated carbanilides, o-phenylphenol, salicylic acid anilide, 2,2'-methylene-bis(4-chlorophenol), tetraaliphatic ammonium bromides or chlorides, hydroxyquinoline and the like.

Coloring agents include titanium dioxide, and other conventional inorganic pigments, organic pigments, dyes and optical brighteners.

Surface conditioner adjuvants include paper sizing lubricants, such as a fatty acid/polyethylene glycol stearate mixture; swelling agents, such as an amine oxide swelling agent; extenders, such as urea; filler retention aids, such as colloidal silica and methyl cellulose; and the like.

Also, as discussed below, an emulsifier may also be optionally present in an amount of between about 0.001% to 3% by weight in the emulsion.

Thus, suitable aqueous emulsions for topical application contain:

(a) 0.01 to 5% by weight of the amine salt;
(b) 0 to 3% by weight emulsifier;
(c) 0 to 5% water repellant assistant, filler, bacteriostat, coloring agent or surface conditioner adjuvant;
(d) 0 to 10% sizing agent, and
(e) the remainder water.

These emulsions are applied to the surface of the cellulosic or natural or synthetic polyamide material by conventional techniques, including padding, spraying, coating, washing, and brushing. After application, the treated surface is dried, with or without an intermediate washing stage. The resulting surface is thus rendered water and oil resistant.

For use as an internal sizing agent to obtain oil and water repellency, the dilution of the instant aqueous emulsions advantageously contain from about 0.0005 to 0.2% by weight of the instant amine salts. The emulsions for dilution may be prepared as a concentrate containing between 5% and 40% by weight, preferably 15 to 25% by weight, of the amine salt, based on the amount of water.

In order to insure emulsion stability of the amine salt in the aqueous medium, the emulsion is advantageously prepared in the presence of a conventional emulsifier. Suitable emulsifiers include cationic, anionic, amphoteric and non-ionic emulsifiers. It is preferred to use non-ionic emulsifiers, such as block copolymers of ethylene oxide and propylene oxide.

The amount of emulsifier used, will, of course depend upon the emulsification characteristics of the amine salt chosen, as well as the desired concentration of the amine salt in the aqueous medium. Where concentrated emulsions are desired, having between 10 and 40% by weight of the amine salt, it is convenient to use up to 5% of emulsifier. In many cases, little or no emulsifier need be added to obtain a stable, aqueous emulsion.

Preferably, when present, the emulsifier is present in the emulsion concentrate in an amount between 0.01 and about 3% by weight.

Suitable emulsifiers for use in the present invention include conventional cationic emulsifiers which are compatible with the active amine salts of the di-perfluoroalkyl group acids, and conventional nonionic emulsifiers.

Preferred emulsifiers are non-ionic emulsifiers including ethoxylated long chain aliphatic amines, ethoxylated long chain aliphatic esters, ethers and thioethers, ethoxylated alkylphenols, block copolymers of ethylene oxide and propylene oxide, and block copolymers of ethylene oxide and propylene oxide on an alkylene polyamine.

Most preferred nonionic emulsifiers are ethylene oxide/propylene oxide block copolymers, polyethoxylated octyl and nonyl phenols, and block copolymers of ethylene oxide and propylene oxide on ethylene diamine. Suitable nonionic emulsifiers are widely commercially available, such as Pluronics, including Pluronic F-68, F-87 and F-98 from BASF Wyandotte Corp., Tritons, including Triton X-35 and X-114 from Rohm and Haas Corp.; Igepals; including Igepal CO-710 and CO-730 from GAF Corp.; and Tetronics, such as Tetronic 904, from BASF Wyandotte Corp.

Pluronics are prepared by condensing ethylene oxide with a hydrophobic base formed by the condensation of propylene oxide with propylene glycol and may be represented empirically by the formula:

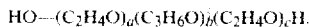

Pluronic F-68 contains about 80% ethylene oxide units ($C_2H_4O$) and the molecular weight of the polypropylene oxide block ($C_3H_6O$)$_b$ is about 1,750. Pluronic F-87 contains about 70% ethylene oxide units ($C_2H_4O$) and the molecular weight of the polypropylene oxide block ($C_3H_6O$)$_b$ is about 2,250. Pluronic F-98 contains about 80% ethylene oxide units ($C_2H_4O$) and the molecular weight of the polypropylene oxide block ($C_3H_6O$)$_b$ is about 2,750.

Triton nonionic alkylphenol surfactants are ethoxylated t-octylphenols or ethoxylated nonylphenols. Triton X-35 is an ethoxylated octylphenol having 3 ethylene oxide units and Triton X-114 is likewise an ethoxylated octylphenol having 7 to 8 ethylene oxide units. Igepal CO-710 is an ethoxylated nonylphenol having 71% combined ethylene oxide units by weight of nonylphenol and Igepal CO-730 is an ethoxylated nonylphenol having 73% combined ethylene oxide units by weight of nonylphenol.

Tetronic 904 is an ethylenediamine/propylene oxide ethylene oxide adduct of the approximate formula

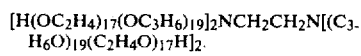

While the instant aqueous emulsions are suitable for rendering a variety of cellulosic and natural and synthetic polyamide materials oil and water repellant, the instant emulsions are particularly advantageous in rendering articles made from paper pulp, such as paper trays, paper plates and analogous paper articles, both oleophobic and hydrophobic.

In order to further increase the efficiency of application of the emulsion to the paper pulp, it is desirable to pre-treat the paper pulp with a cationic agent, such as cationically modified starch, which is adsorbed by the paper pulp and, consequently, tends to increase the amount of fluorochemical transferred from the aqueous emulsion to the cellulose substrate.

Suitable cationic agents, conventionally used to pre-treat cellulose materials such as paper pulp, include conventional cationic modified starches, such as Interbond C, Lok-Size 30, Cato 2, Cato 15 and Cato 17; cationic modified aminoplast resins such as Kymene 557 from Hercules Inc.; cationic polymers such as Santo-Res 21 from Monsanto or Reten-210 from Hercules Inc.; and cationic blocked polyurethanes such as Hypol WB-4000 from W. R. Grace Inc.

Cationic starches are prepared by reacting the starch with amines or quaternary ammonium compounds. Thus, amino ethers of starch are produced by reacting starch with a dialkylaminoalkyl halide which has the amino group in the beta-position, as disclosed, for example, in U.S. Pat. No. 2,970,140 and Canadian Pat. No. 699,812, both of which describe useful cationic starches. Further useful cationic starches are described in U.S. Pat. Nos. 2,876,217 and 3,346,563.

Jointly with the gem-perfluoroalkyl group containing acid salts of the invention, can be added one or more of wide choice of water proofing sizing agents selected from classes such as alkyl anhydrides, e.g. Fibron 68; alkyl ketene dimers e.g. Aquapel 360 XC or Hercon 40; polyurethane emulsions, e.g. Graphsize C; acrylic resins, e.g. Carboset; stearyl amine surfactants, e.g., Ethomeen 18/25 complexed with a fatty acid, e.g. stearic acid; Neofat 14, Neofat 47 or Hystrene 9718.

The amount of adjuvant and sizing agent used for treating paper pulp is of the range specified for topical application, supra.

Thus, for internal sizing of paper pulp suitable aqueous emulsions contain:

(a) 0.0005 to 0.1% by weight of the instant amine salts;

(b) 0.00001 to 0.05% by weight emulsifier;

(c) 0 to 5% by weight filler, bacteriostat, fungicide, coloring agent or surface conditioner adjuvant;

(d) 0 to 10% sizing agent; and (e) the remainder water.

The following examples are intended for illustrative purposes only, and are not intended to restrict the scope of the invention in any way. All parts are by weight unless otherwise specified.

EXAMPLES

The following paragraphs describe the preparation of a number of ammonium and amine salts of gem-bis-perfluoroalkyl acids and their usefulness in imparting oil and water repellency to a variety of substrates.

The preparation of many of these useful fluorinated acids is described in U.S. Pat. No. 4,239,915 (R. A. Falk; assigned to Ciba-Geigy Corporation).

A number of other related acids can also be prepared such as:

4,4-Dimethyl-5,5-bis(1,1,2,2,-tetrahydro perfluorodecylthio)-pentanoic acid

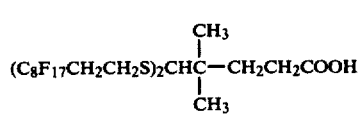

1,1,2,2-tetrahydroperfluoroalkyldecane-thiol (192 g, 0.4 mole), 4-methyl-4-formylo-pentanoic acid (28.8 g, 0.2 mole), and 100 g of toluene were added to a 500 ml Erlenmeyer flask equipped with a magnetic stirring bar. Anhydrous hydrogen chloride was bubbled through the solution for 2 hours and the reaction mixture was then stirred overnight. The white precipitate which formed was collected and washed with methanol/water (1:1), filtered and dried (183 g, 84% yield, m.p. 83°–85° C.).

Analysis for $C_{27}H_{20}F_{34}O_2S_2$: calc.: C: 29.83%, H: 1.84%, F: 59.48%; found: C: 29.93%, H: 1.67%, F: 58.91%.

$^1$H-NMR spectrum: 1.08 ppm(s), 1.87 ppm(m), 2.05–3.15 (m), 3.52 ppm(s), 10.8(s) in a ratio of approx. 6:2:10:1:1

4-Carboxy-benzaldehyde-bis-(1,1,2,2-tetrahydroperfluorodecylthio)-acetal

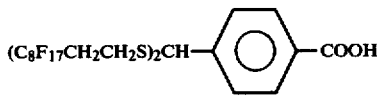

1,1,2,2-tetrahydroperfluorodecane-thiol (48 g, 0.1 mole), 4-carboxy-benzaldehyde (7.5 g, 0.05 mole) and 120 g of toluene were added to a 500 ml Erlenmeyer flask equipped with a magnetic stirring bar. Anhydrous hydrogen chloride was bubbled through the solution for 2 hours. The white precipitate which resulted was collected by filtration, washed with methanol/water (1:1), filtered again, and dried. (54 g, 99% yield, m.p. 134°–136° C.).

Analysis for $C_{28}H_{14}F_{34}O_2S_2$; calc.: C: 30.77%, H: 1.28%, F: 59.16%; found: C: 30.90%, H: 1.33%, F: 58.33%.

$^1$H-NMR spectrum: 2.85 ppm (m), 5.88 ppm (s), 7.80 (m), 8.14 ppm (m), 10.30 ppm (s) in a ratio of approx. 8:1:2:2:1

In a similar manner, the following compound can be prepared from o-formylphenoxyacetic acid:

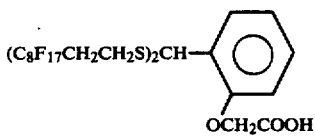

The corresponding sulfoxides and sulfones can be prepared from these gem-bis-perfluoroalkyl-thio acids in the usual way with conventional oxidizing agents such as: hydrogen peroxide, peracetic acid, potassium monopersulfate, m-chloroperbenzoic acid, and the like.

The following examples also describe the preparation of many ammonium and amine salts of a number of these gen-bis-perfluoroalkyl carboxylic acids by conventional means. Additionally, the ammonium and amine salts of this invention can also be prepared by the reaction of ammonium hydroxides or quaternary alkyl ammonium hydroxides with the fluorinated acids. These are shown in examples 1 and 14.

Another alternative method of preparation, is the reaction of the alkali metal salts of the fluorinated acids with quaternary ammonium halides or hydrohalides. Such as the following:

(a) 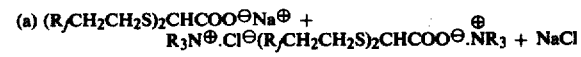

(b) 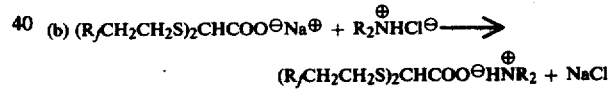

The by-product salts (e.g., NaCl) could be removed by appropriate ion-exchange resins or dialysis membranes.

The examples that follow illustrate a number of the compounds which are included in this invention and their utility. The compounds of this invention are not necessarily limited to those exemplified.

TABLE I

Examples
Gem-perfluoroalkylthio Group Containing Acids

| Designation for subsequent examples | Structure | $R_f$-distribution (%) | | | | |
|---|---|---|---|---|---|---|
| | | $C_6F_{13}$— | $C_8F_{17}$— | $C_{10}F_{21}$— | $C_{12}F_{25}$— | $C_{14}F_{29}$— |
| A$_1$ | $(R_fCH_2CH_2S)_2C(CH_3)CH_2CH_2COOH$ | 6 | 36 | 46 | 11 | 1 |
| A$_2$ | $(R_fCH_2CH_2S)_2C(CH_3)CH_2CH_2COOH$ | 2 | 7 | 71 | 11 | 1 |
| A$_3$ | $(R_fCH_2CH_2S)_2C(CH_3)CH_2CH_2COOH$ | 6 | 30 | 49 | 13 | 2 |
| B | $(R_fCH_2CH_2S)_2CHCOOH$ | 13 | 84 | 3 | — | — |
| C | $(R_fCH_2CH_2S)_2C(COOH)CH_2CH_2COOH$ | 7 | 35 | 46 | 11 | 1 |
| D | $[(CH_3)_2CFOCF_2CF_2CH_2CH_2S]_2C(CH_2CH_3)COOH$ | | | | | |
| E | $[(CH_3)_2CFOCF_2CF_2CH_2CH_2S]_2C(CH_3)CH_2COOH$ | | | | | |
| F | $*(C_6F_{13}CH_2CH_2S)_2C(\phi)CH_2CH_2COOH$ | | | | | |
| G | $(C_8F_{17}CH_2CH_2CH_2CH_2S)_2C(COOH)_2$ | | | | | |
| H | $(C_8F_{17}CH_2CH_2OCH_2CH_2CH_2S)_2C(CH_3)CH_2COOH$ | | | | | |
| I | $[C_8F_{17}(CH_2)_2N(CH_3)(CH_2)_3S]C(CH_3)CH_2COOH$ | | | | | |
| J | $(C_8F_{17}CH_2CH_2S)_2C(CH_3)COOH$ | | | | | |
| K | $(C_6F_{13}CH_2CH_2S)_2C(CH_2CH_2COOH)_2$ | | | | | |

TABLE I-continued

Examples
Gem-perfluoroalkylthio Group Containing Acids

| Designation for subsequent examples | Structure | $R_f$ distribution (%) | | | | |
|---|---|---|---|---|---|---|
| | | $C_6F_{13}$— | $C_8F_{17}$— | $C_{10}F_{21}$— | $C_{12}F_{25}$— | $C_{14}F_{29}$— |
| L | $(C_8F_{17}CH_2CH_2SO_2)_2C(CH_3)CH_2CH_2COOH$ | | | | | |
| M | $(C_8F_{17}CH_2CH_2S)_2CHC(CH_3)_2CH_2CH_2COOH$ | | | | | |
| N | $(C_8F_{17}CH_2CH_2S)_2CH\text{—}\phi\text{—}COOH$ | | | | | |
| O | $(C_8F_{17}CH_2CH_2S)_2\text{—}CH\text{—}\phi\text{—}CH\text{=}CHCOOH$ | | | | | |
| P | $(C_8F_{17}CH_2CH_2S)_2CHCOOH$ | | | | | |

*($\phi$ = phenyl)

EXAMPLES 1–15

This group of examples illustrates a number of the amines and ammonium compounds which are useful for the preparation of the salts of this invention.

Ten gram portions of the fluorochemical acid $A_1$ in table I were weighed into 2 ounce glass jars with the amines listed in Table II, and 30.0 g of methylene chloride. Several stainless-steel balls were added to aid mixing.

The jars were capped, shaken, and placed on a rolling device overnight. The products were then collected by filtration and dried under vacuum at room temperature.

EXAMPLES 16–29

These examples demonstrate how the above salts can be converted into useful emulsions or dispersions.

The $R_f$-acid amine salts listed in the above examples (see table II) were each placed in 2 ounce jars with distilled water, and Pluronic F-68 (wetting aid, from BASF Wyandotte). These mixtures were then stirred at 60°–65° C. for 20 minutes. Several stainless-steel balls were added and the jars were placed on a rolling device overnight. These examples of aqueous dispersions are listed in Table III.

TABLE II

Examples 1–15

| Example | Amine | grams of amine used | approx. mole ratio $R_f$-acid:amine | wgt. of dry salt collected | yield | melting range of salt (°C.) | % Fluorine calc. |
|---|---|---|---|---|---|---|---|
| 1 | ammonium hydroxide 29.4% $NH_4OH$ in water | 1.5 | 1:1 | 10.3 g | 97.7% | 106–108 | 61.0 |
| 2 | monoethanolamine $H_2NCH_2CH_2OH$ | 0.56 | 1:1 | 10.5 g | 99.0 | 110–130 | 59.7 |
| 3 | diethanolamine $HN(CH_2CH_2OH)_2$ | 1.0 | 1:1 | 9.9 g | 89.6 | 104–131 | 57.7 |
| 4 | triethanolamine $N(CH_2CH_2OH)_3$ | 1.37 | 1:1 | 10.7 g | 93.7 | 104–134 | 55.8 |
| 5 | Ethomeen C/25 (Armak) $RN\overset{(CH_2CH_2O)_xH\ R\ =\ coco}{\underset{(CH_2CH_2O)_yH}{}}$ $x + y \approx 15$ | 8.16 | 1:1 | 11.3 g | 62.3 | 86–90 | 36.1 |
| 6 | Ethomeen 18/25 (Armak) $RN\overset{(CH_2CH_2O)_xH\ R\ =\ stearyl}{\underset{(CH_2CH_2O)_yH}{}}$ $x + y \approx 15$ | 8.3 | 1:1 | 11.5 g | 62.7 | 93–94 | 35.8 |
| 7 | Ethoduomeen T-20 (Armak) $RNCH_2CH_2CH_2N$ with $(CH_2CH_2O)_xH$ $R$ = tallow, $(CH_2CH_2O)_zH$, $(CH_2CH_2O)_yH$ $x + y + z \approx 10$ | 1.97 | 1:0.5 | 9.4 g | 78.3 | 99–103 | 53.2 |
| 8 | Jeffamine ED-900 (Jefferson) $H_2NCHCH_2(OCH_2CH)_a(OCH_2CH_2)_b(OCH_2CH)_cNH_2$ with $CH_3$ groups ~76% ethylene oxide, M.W. = 980 | 4.5 | 1:0.5 | 8.9 g | 61.1 | 83–85 | 44.6 |
| 9 | Jeffamine ED-2001 (Jefferson) same as ED-900 except 88% ethylene oxide | 10.8 | 1:0.5 | 16.5 g | 79.1 | 90–96 | 31.6 |

TABLE II-continued

Examples 1-15

| Example | Amine | grams of amine used | approx. mole ratio R$_f$ acid:amine | wgt. of dry salt collected | yield | melting range of salt (°C.) | % Fluorine calc. |
|---|---|---|---|---|---|---|---|
| 10 | DMAMP-80 (IMC) $(CH_3)_2-C-CH_2OH$ 80% in water $\quad\quad N(CH_3)_2$ | 1.34 | 1:1 | 9.3 g | 82.1 | 87–91 | 57.7 |
| 11 | AMP (IMC) $(CH_3)_2-C-CH_2OH$ $\quad\quad NH_2$ | 0.41 | 1:0.5 | 10.3 g | 99.3 | 99–115 | 60.6 |
| 12 | tetrasodium EDTA $NaOOCCH_2\diagdown\quad\quad/CH_2COONa$ $\quad\quad NCH_2CH_2N$ $NaOOCCH_2/\quad\quad\diagdown CH_2COONa$ | 3.81 | 1:1 | 13.5 g | 97.8 | >220 | 51.1 |
| 13 | tetrasodium EDTA same as above | 1.91 | 1:0.5 | 11.7 g | 98.3 | >220 | 52.7 |
| 14 | tetramethylammonium hydroxide $(CH_3)_4NOH$ (20% in methanol) | 4.17 | 1:1 | 8.9 g | 63.0 | 159–164 | 60.5 |
| 15 | Quadrol (BASF-Wyandotte) $\quad CH_3\quad\quad\quad\quad\quad\quad CH_3$ $\quad\;\;\mid\quad\quad\quad\quad\quad\quad\quad\mid$ $HO-CH-CH_2\diagdown\quad\quad CH_2CHOH$ $\quad\quad\quad\quad\quad N-CH_2CH_2-N$ $HO-CH-CH_2/\quad\quad CH_2CHOH$ $\quad\;\;\mid\quad\quad\quad\quad\quad\quad\quad\mid$ $\quad CH_3\quad\quad\quad\quad\quad\quad CH_3$ | 1.34 | 1:0.5 | 9.8 g | 86.2 | 89–101 | 56.0 |

TABLE III

Examples 16–29

Aqueous Dispersions of $(R_f CH_2CH_2S)_2C-CH_2CH_2COOH$·Amine Salts
$\quad\quad\quad\quad\quad\quad\quad\quad\quad\quad\quad\quad\quad\quad\;\;\mid$
$\quad\quad\quad\quad\quad\quad\quad\quad\quad\quad\quad\quad\quad\quad CH_3$

| Example | made from | weight of dist. water | weight of 10% solution of Pluronic F-68 | calculated solids content | Appearance of dispersion | pH of a 1% dilution (w/v) in water |
|---|---|---|---|---|---|---|
| 16 | 4.0 g example 1 salt (ammonium hydroxide) | 34.0 g | 3.0 g | 10.5% | free flowing, opalescent liquid | 8.6 |
| 17 | 4.0 g example 2 salt (monoethanolamine) | 16.5 g | 3.0 g | 18.3% | free flowing, translucent | 10.0 |
| 18 | 4.0 g example 3 salt (diethanolamine) | 16.5 g | 3.0 g | 18.3% | free flowing, translucent liquid | 9.1 |
| 19 | 4.0 g example 4 salt (triethanolamine) | 22.9 g | 3.0 g | 14.4% | free flowing, translucent liquid | 7.2 |
| 20 | 4.0 g example 5 salt (Ethomeen c/25) | 16.0 g | none | 20.0% | free flowing, milky white liquid | 7.7 |
| 21 | 4.0 g example 6 salt (Ethomeen 18/25) | 16.0 g | none | 20.0% | free flowing, milky white liquid | 9.0 |
| 22 | 4.0 g example 7 salt (Ethoduomeen T-20) | 16.3 g | 3.0 g | 18.5% | pale-yellow cream | 6.5 |
| 23 | 4.0 g example 8 salt (Jeffamine ED-900) | 27.5 g | 0.5 g | 12.7% | free flowing, opalescent liquid | 8.7 |
| 24 | 4.0 g example 9 salt (Jeffamine ED-2001) | 19.5 g | none | 17.0% | free flowing, opalescent liquid | 9.7 |
| 25 | 4.0 g example 10 salt (DMAMP) | 40.0 g | 3.0 g | 9.2% | fairly viscous opalescent liquid | 9.2 |
| 26 | 4.0 g example 11 salt (AMP) | 28.2 g | 3.0 g | 12.2% | opaque viscous liquid | 9.5 |
| 27 | 4.0 g example 12 salt (Na$_4$ EDTA) | 28.2 g | 3.0 g | 12.3% | opalescent viscous liquid | 9.5 |
| 28 | 4.0 g example 14 salt (tetramethyl ammonium hydroxide) | 16.5 g | 3.0 g | 18.3% | fairly viscous opalescent liquid | 9.5 |
| 29 | 4.0 g example 15 salt (Quadrol) | 16.4 g | 3.0 g | 18.4% | fairly viscous opaque liquid | 9.8 |

EXAMPLE 30

A 1.00 g sample of $(R_f CH_2CH_2S)_2CHCOO^- \ ^+N(CH_3)_4$ was made into an aqueous dispersion, in the same manner as examples 16–29, with: 4.02 g dist. water, 0.10 g diethanolamine, and 0.75 g of a 10% solution of Pluronic F-68 (wetting aid).

$R_f = 6\% \ C_6F_{13}, 36\% \ C_8F_{17}, 46\% \ C_{10}F_{25}, 1\% \ C_{14}F_{29}$.

EXAMPLE 31

By an alternative method, the salt and dispersion were formed simultaneously, in one operation, by weighting 6.84 g dist. water, 0.17 g diethanolamine, 1.20 g of 10% ag. Pluronic F-68, and 1.59 g acid B (in Table I) into a 2 ounce jar. The contents were stirred at 60° C. for 10 min. The jar was capped and placed on a rotating device for several days. A viscous, slightly cloudy liquid resulted. At 1% in water, the pH was 10.0.

EXAMPLES 32–37

Several dispersing and/or wetting aids were utilized in these examples which are listed in table IV. Two grams of acid $A_2$ from table I, 0.162 g diethanolamine, and the amount and type of wetting aid shown in table IV were mixed with 2 grams of distilled water at 55° C.; then diluted with additional water (see table IV). After additional mixing at 55° C.; the dispersions, in 2 ounce jars, were rotated overnight.

EXAMPLE 38

In this example, the salt and dispersion were also prepared in one operation.

To a 20-liter glass reactor, equipped with a motor driven stirrer, thermometer, nitrogen inlet, and vent; were charged 1755 g dist. water and 195 g Pluronic F-68 (powder). This was stirred at 35°–40° C. until dissolved. Then 273.3 diethanolamine (2.60 moles) and 8900 g dist. water were added with stirring. Then 3702 g of a paste containing 74% acid $A_3$ from table I in water and methanol (2.25 moles) was charged in followed by 174.4 g dist. water. The mixture was stirred at 60°–65° C. for 4 hours. A viscous, light-straw colored, translucent liquid resulted.

Solids: calculated = 21.3%, found = 21.5%; fluorine in solids: calculated = 53.0%, found = 53.50%.

The above dispersion formed a clear bluish solution when diluted to 1% (as is) in dist. water, pH = 9.7.

TABLE IV

Examples 32–37

Dispersing/wetting aids for 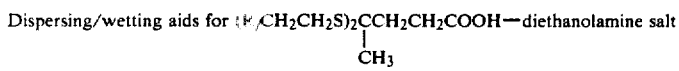—diethanolamine salt

| Example | Dispersing/wetting aid amount* | trade-name | type | additional water added | total batch size | Appearance of dispersion |
|---|---|---|---|---|---|---|
| 32 | mix { 0.62 g / 1.38 g | Tetronic 504 Tetronic 701 (BASF-Wyandotte) | propylene oxide-ethylene oxide adducts of ethylene diamine | 6.36 g | 12.52 g | white paste |
| 33 | 1.0 g | Triton X-35 (Rohm & Haas) | octylphenoxy polyethoxyethanol | 12.64 g | 17.8 g | white paste |
| 34 | 1.0 g | Triton X-114 | octylphenoxy polyethoxyethanol | 12.64 g | 17.8 g | somewhat viscous, free-flowing, hazy liquid |
| 35 | 1.0 g | Pluronic F-68 (BASF-Wyandotte) | ethylene oxide, propylene oxide, ethylene oxide block polymers | 12.64 g | 17.8 g | somewhat viscous, free-flowing, hazy liquid |
| 36 | 1.0 g | Pluronic F-87 | ethylene oxide, propylene oxide, ethylene oxide block polymers | 12.64 g | 17.8 g | somewhat viscous, free-flowing, hazy liquid |
| 37 | 1.0 g | Pluronic F-127 | ethylene oxide, propylene oxide, ethylene oxide block polymers | 12.64 g | 17.8 g | somewhat viscous, free-flowing, hazy liquid |

*Weight of 10% (w/v) solutions in water.

EXAMPLES 39–42

Aqueous dispersions of acid $A_3$ (listed in table I) were made with several other amines. The preparation of the salts and dispersions were carried out in one operation. These examples are listed in table V. Distilled water, the amine, wetting aid, and fluorinated acid were blended together in a 2 ounce jar, stirred for 10 min. at 60° C., and placed on a rotating device overnight.

EXAMPLE 43

The use of another of the fluorinated acids is described in this example.

By the method described in Example 31, a dispersion was prepared from 7.92 g dist. water, 0.34 g diethanolamine, 2.0 g of a 10%. aq. Pluronic F-98 solution, and 2.0 g of acid C in Table 1. An opalescent liquid resulted.

EXAMPLE 44–51

The use of a number of other fluorinated acids and amines is described in this group of examples.

Using the methods and techniques described in examples 1–29, the examples listed in Table VI are prepared.

TABLE V

Examples 39-42

| Example | Wgt. of $R_f$-acid | Wgt. of water | Wgt. of Pluronic F-68* | Amine amount | Amine type | Dispersion calc. % solids | Dispersion appearance | pH of a 1% dilution in water |
|---|---|---|---|---|---|---|---|---|
| 39 | 4.0 g | 15.96 g | 3.0 g | 0.54 g | triethanolamine | 20.6 | free-flowing, milky white liquid | 10.0 |
| 40 | 4.0 g | 16.18 g | 3.0 g | 0.32 g | AMP (IMC) 2-amino-2-methyl-1-propanol | 19.7 | slightly viscous, opalescent liquid | 9.5 |
| 41 | 4.0 g | 15.50 g | 3.0 g | 1.00 g | Diam-G21 (Henkel) N—coco-1,3-propane diamine | 22.6 | viscous, creamy white liquid | 10.2 |
| 42 | 4.0 g | 15.22 g | 3.0 g | 1.28 g | Ethomeen T-12 (Armak) bis-(2-hydroxyethyl)-tallowamine | 23.7 | separated | — |

*As 10% (w/v) solution in water.

TABLE VI

Examples 44-51

| Example | $R_f$-acid as listed in Table I | Amine | Product |
|---|---|---|---|
| 44 | D | stearyl amine | $[(CF_3)_2CFOCF_2CF_2CH_2CH_2S]_2C(CH_2CH_3)COO^\ominus . H_3N^\oplus - C_{18}H_{37}$ |
| 45 | E | diethylamine | $[(CF_3)_2CFOCF_2CF_2CH_2CH_2S]_2C(CH_3)CH_2COO^\ominus . H_2N^\oplus(CH_2CH_3)_2$ |
| 46 | F | guanidine | $[(C_6F_{13}CH_2CH_2S)_2C(phenyl)CH_2CH_2COO^\ominus]_2 . (H_3N^\oplus)_2C=NH$ |
| 47 | G | triethylamine | $(C_8F_{17}CH_2CH_2CH_2CH_2S)_2C(COO^\ominus)_2 . [HN^\oplus(CH_2CH_3)_3]_2$ |
| 48 | H | pyridine | $(C_8F_{17}CH_2CH_2OCH_2CH_2CH_2S)_2C(CH_3)CH_2COO^\ominus . HN^\oplus\text{-pyridine}$ |
| 49 | I | melamine | $[[C_8F_{17}(CH_2)_2N(CH_3)(CH_2)_3S]C(CH_3)CH_2COO^\ominus]_3 . H_3N^\oplus\text{-melamine}$ |
| 50 | J | poly(ethylenimine) | $[(C_8F_{17}CH_2CH_2S)_2C(CH_3)COO^\ominus]_{180}\overset{\oplus}{N}H_3-(CH_2CH_2N^\oplus H_2)_{179}H$ |
| 51 | K | Duomeen C (Armak) | $(C_6F_{13}CH_2CH_2S)_2C(CH_2CH_2COO^\oplus)_2 . [H_2NCH_2CH_2CH_2N^\oplus\text{—}R]_2 H_2$ where R = coco |

EXAMPLE 52

This example describes the use of a bis-sulfone type of acid.

Using the method described in example 31, a dispersion was prepared from 6.64 g dist. water, 2.20 g of 10% aq. Pluronic F-68, 0.21 g diethanolamine, and 2.00 g of acid L (from table I). A fluid translucent white liquid resulted (at 22.0% solids). A 1% dilution in water produced a hazy solution at pH 9.7.

The following examples illustrate how the compounds and dispersions of the previous examples can be used to impart oil and water repellent properties to a variety of substrates.

APPLICATION EXAMPLES

EXAMPLE 53

Samples of fluorochemical dispersion of the type described in example 38 were added to a 10% aqueous solution of paper maker's starch (pH adjusted to 9.6 with 10% aq. NaOH). This starch solution was applied to unsized paper by padding (paper dipped through starch solution, then passed through single nip rollers). The resulting sheets of paper were dried at ambient conditions for 15 minutes, then for 3 minutes at 200° F. in an "Emerson Speed Drier" (heated metal plate with canvas cover). Table VII lists the results.

TABLE VII

Example 53

| | amount of fluorochem dispersion added[1] | dry weight pick-up of starch | amount of fluorochem. solids to wgt. of paper | oil kit num- ber[2,3] | Gurley-Cobb test - water absorbed[2,4] |
|---|---|---|---|---|---|
| a | none | 5.8% | none | 0 | 121. g/M² |
| b | 6 ml | 5.2% | 0.036% | 5 | 12.8 g/M² |
| c | 8 ml | 4.2% | 0.039% | 6 | 13.7 g/M² |
| d | 10 ml | 5.1% | 0.060% | 6 | 12.6 g/M² | notes:
[1] amount shown was pre-diluted 1:1 with dist. water and added into 100 ml starch solution at 150° F.
[2] measured on side facing canvas in drier.
[3] OIL KIT for Surface Oil Resistance Tests (TAPPI method UM-557)
[4] Cobb size test, ASTM method D-3285-73; measurements made after 15 second exposure to water.

An easily made kit of twelve solutions of varying proportions of Castor Oil, Toluene, and Heptane is useful in comparing *surface oil resistance.*

| Kit No. | Volume Castor Oil | Volume Toluene | Volume Heptane |
|---|---|---|---|
| 1 | 200 | 0 | 0 |
| 2 | 180 | 10 | 10 |
| 3 | 160 | 20 | 20 |
| 4 | 140 | 30 | 30 |
| 5 | 120 | 40 | 40 |
| 6 | 100 | 50 | 50 |
| 7 | 80 | 60 | 60 |
| 8 | 60 | 70 | 70 |
| 9 | 40 | 80 | 80 |
| 10 | 20 | 90 | 90 |
| 11 | 0 | 100 | 100 |
| 12 | 0 | 90 | 110 |

The "kit value" is defined as the highest number solution that will stand on the surface of the plate for 15 seconds in the form of drops without failing. Failure is detected by pronounced darkening caused by penetration. The darkening of even a small fraction of the area under the drop is considered failure.

EXAMPLE 54

A 4% solution of cationic starch in distilled water was prepared by cooking in a double boiler. When cooled, 50 ml of this starch solution was placed into a beaker followed by 50 ml of a 2% as is (0.426% solids) solution of fluorochemical dispersion of the type described in example 38. This mixture was then pad applied (as is example 53) to unsized, bleached, kraft paper at 100% wet pick-up. The resulting paper was dried (as in example 53) at 220° F. for 20 minutes. The treated paper demonstrated an oil kit number (TAPPI UM-557) of 12 and a Gurley-Cobb sizing value of 24 gm/M$^2$ of water absorbed, compared to a kit number of 0 and Cobb test of 183 g/M$^2$ with cationic starch alone with no fluorochemical.

EXAMPLE 55

This example demonstrates the utility of these dispersions as internal sizes.

Six grams of dry bleached Kraft pulp were diluted in 289 ml distilled water and thoroughly dispersed in a blender. To this pulp slurry was added 3.6 ml of a 1% dilution (as is) of the dispersion from example 31 in distilled water. This was mixed in for 5 minutes, then 6 ml of a 1% aqueous solution of cooked cationic starch was added. This was mixed together for an additional 5 minutes. To this, 1.2 ml of a 1.5% (on solids) dilution of an alkyl ketene dimer emulsion was added as a water repellent adjuvant. This was mixed in for another 10 minutes. The resulting slurry was diluted with an additional 500 ml of dist. water and mixed again. This mixture was then poured over a 100 mesh wire screen, with a vacuum applied from below which pulled the water from the pulp mixture to form a sheet on the screen. The wet sheet was removed from the screen and dried between another screen and hard surface at a pressure of approximately 0.4 lbs/in.$^2$ at 110° C. for 1½ hours. The paper formed in this manner, showed a TAPPI method UM-557 oil kit number of 4 (see example 53). One ml of hot (110° C.) corn oil placed on the paper remained on the surface and did not penetrate for 12 minutes. Similarly, 1 ml of hot (80° C.) water containing 0.5% of Triton X-165 wetting agent (from Rohm & Haas) placed on the paper did not penetrate for 20 minutes. Whereas, paper made in the same manner, including the cationic starch and water repellant adjuvant but without the fluorochemical dispersion; demonstrated an oil kit number of <1, and held the hot corn oil and hot water/Triton X-165 solution for less than one minute (began to penetrate as soon as applied).

EXAMPLES 56–58

Three pad bath solutions were made up, each containing: 8.6 ml of the same kind of fluorochemical dispersion as described in example 38, 2.5 ml of Aerotex M-3 textile resin (at 80% actives, from American Cyanamid), 0.4 ml Aerotex Accelerator UTX, 0.1 ml Mykon NRW-3 (wetting agent from Sun Chemical), and 88.4 ml distilled water.

These pad baths were then applied to the substrates shown in table VIII at a 50% wet pickup (one pass through bath into single nip rollers). The treated samples were dried at 110° C. for 2 minutes and cured at 163° C. for 3 minutes. Water and oil repellency measurements were then made. The results are shown in Table VIII. Application of the same system without the fluorochemical dispersion resulted in no oil or water repellency (zero ratings).

TABLE VIII

| | Examples 56–58 | | |
|---|---|---|---|
| Example | Substrate | Oil Repellency Rating[1] | Water Repellency Rating[2] |
| 56 | fiber reinforced cellulose based non-woven fabric | 5 | 50 |
| 57 | 100% filament Nylon poncho | 4 | 90 |
| 58 | 100% spun Dacron | 4 | 80– |

[1]Oil Repellency: AATCC test method no. 118-1975
[2]Water Repellency: AATCC test method no. 22-1974

EXAMPLES 59–63

For purposes of comparison, mono-perfluoroalkyl chain containing carboxylic acid compounds and a sample of a commercial fluorochemical paper size (3M's FC-807, twin-R$_f$-tailed phosphate ester, ammonium salt) were tested against the gem-bisperfluoroalkylthio group containing acids of this invention (examples 59–62). The compounds were applied aqueous dispersions or solutions and evaluated in a manner to that described in example 55 (i.e. internal size). These tests are shown in table IX.

TABLE IX

| | | Examples 59–63 | | | | Hold-out tests* | |
|---|---|---|---|---|---|---|---|
| Example | Fluorochemical | fluorine on wgt. of paper | cationic starch in paper | alkyl Ketene dimer adjuvant in paper | oil Kit number | hot, 110° C. corn oil | hot, 80° C. water + 0.5% Triton X-165 |
| 59 | diethanolamine salt of $(C_8F_{17}CH_2CH_2S)_2C(CH_3)CH_2CH_2)COOH$ aqueous dispersion prepared as in example 31 | 0.08% | 1.0% | 0.3% | 5 | >20 min. | 20 min. |

TABLE IX-continued

| | | Examples 59-63 | | | Hold-out tests* | |
|---|---|---|---|---|---|---|
| Example | Fluorochemical | fluorine on wgt. of paper | cationic starch in paper | alkyl Ketene dimer adjuvant in paper | oil Kit number | hot, 110° C. corn oil | hot, 80° C. water + 0.5% Triton X-165 |
| 60 | diethanolamine salt of $C_8F_{17}CH_2CH_2SCH_2CH_2COOH$, aqueous solution | " | " | " | 1-2 | <1 min. | <1 min. |
| 61 | diethanolamine salt of $C_8F_{17}CH_2CH_2SCH_2COOH$, aqueous solution | " | " | " | 2 | 2 min. | 3 min. |
| 62 | aqueous dispersion of the same type as in example 38 (diethanolamine salt of acid $A_3$ in table I) | 0.04% " 0.06% " | " " " " | 0.3% 0.45% 0.3% 0.45% | 4 3-4 5 5 | 20 min. >20 min. >20 min. >20 min. | 20 min. 15-20 min. 20 min. 20 min. |
| 63 | Scotchban FC-807 (3M Co.) bis-perfluoroalkyl phosphate ester, ammonium salt | 0.04% " 0.06% " | " " " " | 0.3% 0.45% 0.3% 0.45% | 2-3 3 5 4 | <1 min. <1 min. >20 min. >20 min. | 15-20 min. 15-20 min. 20 min. >20 min. |

*Hold-out tests observed for up to 20 minutes.

EXAMPLE 64

In this example, the salt of the sulfone type acid (L) was evaluated as an internal paper size.

The fluorochemical dispersion of example 52 was applied and tested by the method described in example 55. At an application level of 0.78% dispersion to weight of dry pulp; an oil kit value of 5 was obtained, the sheet held out the hot corn oil for more than 20 minutes, and held out the hot water+Triton X-165 solution for about 20 minutes.

EXAMPLE 65

In this example, the salt of another acid (M) was also evaluated as an internal size.

By the method described in Example 31, a dispersion was prepared from 14.05 g dist. water, 3.00 g of 10% aq. Pluronic F-68, 0.43 g diethanolamine, and 4.00 g of acid M (from Table I). This produced a translucent white paste (22% solids). At 1% in water, the pH was 9.5.

This fluorochemical dispersion was then evaluated by the method of example 55. It showed the same performance as listed in example 64.

EXAMPLE 66

By the method described in example 54, the dispersion from example 65 (acid M) was evaluated as an external paper size. A mixture of 50 ml of 4% cationic starch, 20 ml of the fluorochemical dispersion (diluted to 5% as is), and 30 ml dist. water were pad applied to the paper. The dried sheet showed an oil Kit number of 9, and a Gurley-Cobb sizing value of 57 g/M² (water absorbed).

EXAMPLE 67

In this example, the dispersion of acid N (from table 1) was prepared and evaluated as an external paper size.

By the method described in example 31, an aqueous fluorochemical dispersion was prepared from 14.03 g dist. water, 3.00 g of a 10% solution of Pluronic F-68, 0.42 g of diethanolamine, and 4.00 g of acid N (aromatic type). The resulting product was a milky white (almost translucent paste)—giving a pH of 9.28 at 1% in water.

This was applied and tested as above (example 66). The dried sheet of paper had an oil Kit number of 6 and a Curley-Cobb sizing value of 80 g/M².

EXAMPLE 68

In this example, an aqueous dispersion was prepared from acid P (in table I) and also evaluated as an external size on paper.

By the method described in example 31; 14.16 g of dist. water, 3.00 g of a 10% solution of Pluronic F-68, 0.46 g of diethanolamine, and 4.00 g of acid P (with 61.87% F found) were combined to form a translucent light-straw colored liquid which had a pH of 9.07 when diluted to 1% in water.

When applied and tested as in example 66, the resulting treated paper had an oil Kit value of 3 and a Cobb-size rating of 103 g/M² (water absorbed).

EXAMPLE 69

In this example the acid of the formula

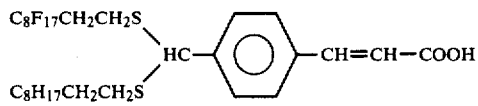

was prepared by the following procedure:

p-Formylcinnamic acid, 15.0 g (0.085 moles), n-$C_8F_{17}CH_2CH_2SH$, 82.5 g (0.17 moles) and acetic acid, 200.0 g, were charged to the reaction flask and the temperature was raised and held at 81° C. to dissolve the p-formylcinnamic acid. Hydrogen chloride gas was introduced for 10 minutes during which time a white solid precipitated out of solution. The resulting solids were filtered, washed with aqueous methanol and dried in a 60° C. vacuum oven overnight. The yield was 95.9% of white powder.

Elemental analysis:

| | % calculated | % found |
|---|---|---|
| C | 32.21 | 32.34 |
| H | 1.44 | 1.32 |
| F | 57.75 | 56.83 |
| S | 5.73 | 6.55 |

EXAMPLE 70

As in Example 68, an aqueous emulsion was prepared from 13.77 g dist. water, 4.40 g of a 10% solution of Pluronic F-68, 0.56 g diethanolamine, and 4.00 g of acid ")", listed in table I, and prepared in accordance with Example 69. This produced a white liquid which had a pH of 9.3 at 1% in water.

When applied and tested as above, the treated paper had an oil kit number of 8 and a Cobb-size value of 17 g/M² (water absorbed).

What is claimed is:

1. A compound of the formula

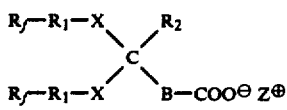

wherein $R_f$ is perfluoroalkyl of 6 to 14 carbon atoms;
$R_1$ is straight or branched chain alkylene of 2 to 8 carbon atoms;
X is —S— or —SO$_2$—;
$R_2$ is hydrogen or alkyl of 1 to 4 carbon atoms;
B is a covalent bond or alkylene of 1 to 6 carbon atoms; and
Z is the cation of mono-, di-, or tri-ethanolamine.

2. A compound according to claim 1 wherein $R_f$ is perfluoroalkyl of 6 to 12 carbon atoms, $R_1$ is alkylene of 2 to 4 carbon atoms, and $R_2$ is hydrogen or alkyl of 1 to 2 carbon atoms.

3. A compound according to claim 1 wherein Z is the cation of diethanolamine.

4. A compound according to claim 2 wherein Z is the cation of diethanolamine.

* * * * *